United States Patent [19]

Nagatoki

[11] 4,090,517
[45] May 23, 1978

[54] MEDICAL APPLIANCE

[76] Inventor: Nagatoki Takenaka, 10-14, 1-chome, Shiba-Kubo-cho, Tanashi-shi, Tokyo-To, Japan, 188

[21] Appl. No.: 736,086

[22] Filed: Oct. 27, 1976

[30] Foreign Application Priority Data

Jul. 1, 1976 Japan .................................. 51-87053

[51] Int. Cl.² ........................................... A61B 17/36
[52] U.S. Cl. ................................. 128/303.1; 128/399
[58] Field of Search ................. 128/303.1, 24.1, 172.1, 128/254, 255, 405, 407–409, 329 A, 399–401; 219/238, 239, 236, 227

[56] References Cited

U.S. PATENT DOCUMENTS

| 973,592 | 10/1910 | Aller | 219/239 |
| 1,076,210 | 10/1913 | Kerr et al. | 128/172.1 |
| 1,353,965 | 9/1920 | Kuhn et al. | 219/238 X |
| 3,207,159 | 9/1965 | Tateisi | 128/303.1 |
| 3,625,202 | 12/1971 | Oyoshirhara et al. | 128/329 A X |

FOREIGN PATENT DOCUMENTS

| 1,108,919 | 1/1956 | France | 128/303.1 |
| 1,466,955 | 5/1969 | Germany | 219/227 |
| 37-4190 | 3/1962 | Japan | 128/303.1 |

Primary Examiner—Robert W. Michell
Assistant Examiner—Lee S. Cohen
Attorney, Agent, or Firm—Otto John Munz

[57] ABSTRACT

Medical appliance for moxibution, comprising a hand-held housing enclosing an electric heater and a temperature control device therefor. A number of presser elements of various shapes are interchangeably secured to the housing to extend from one end thereof and are in thermal contact with a plate-like element heated by the heater. Each presser element is supplied with a cover of heat-insulating material shaped to fit over and about the exposed portion thereof.

7 Claims, 11 Drawing Figures

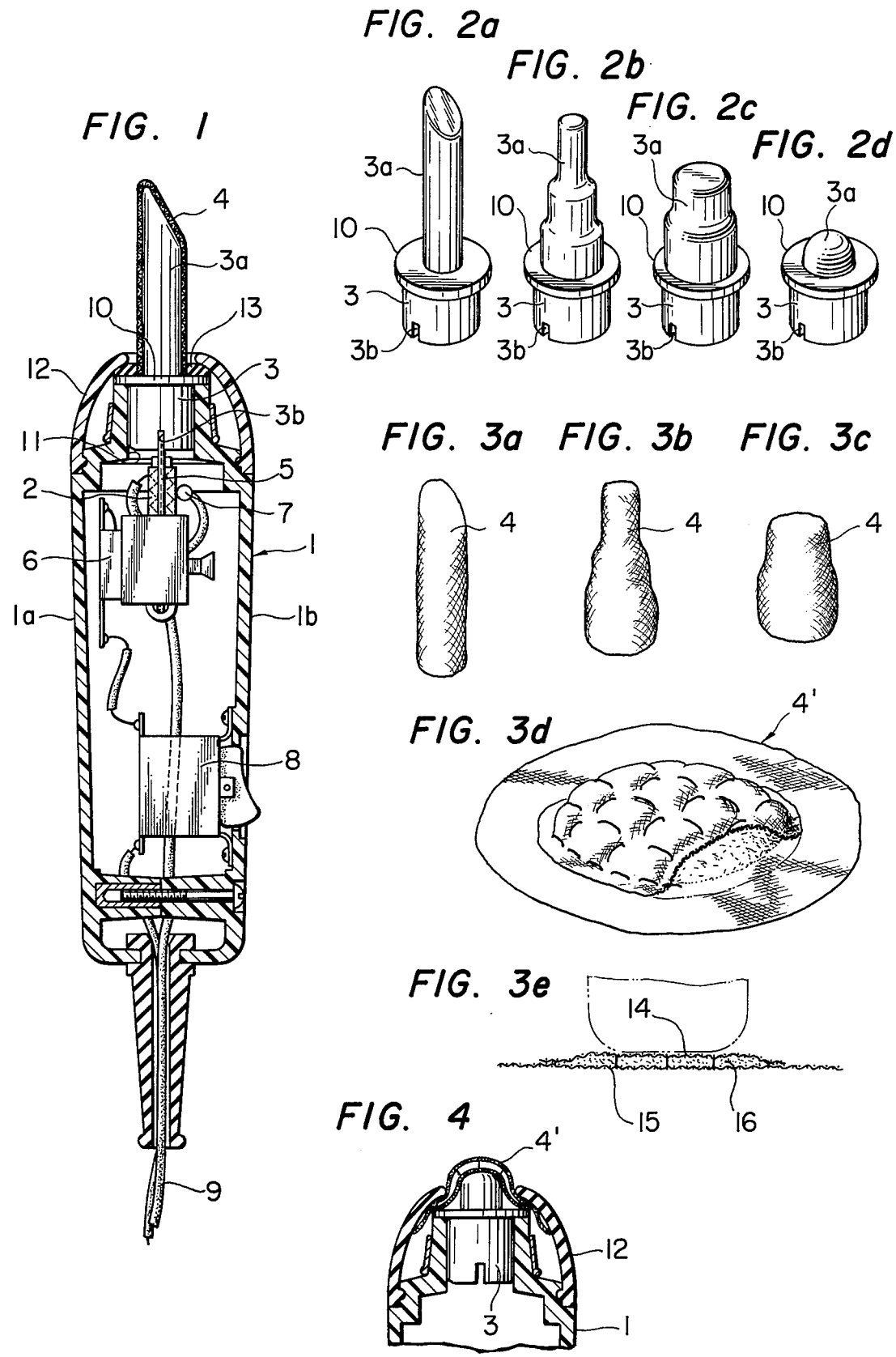

MEDICAL APPLIANCE

BACKGROUND OF THE INVENTION

1. Field of the Invention

This invention relates to a medical appliance used in oriental medicine, particularly an appliance for stimulating specified parts of the human body mainly in the form of thermal stimulus.

2. Description of the Prior Art

In oriental medical science, medical treatment is carried out by the use of medical herbs and massage in the same way as Western medical science. However, according to a special theory of oriental medicine there are other special channels in which special humors flow in the human body and the junctions or diverging points of these channels have special characteristics. It is confirmed that these junctions show special body temperatures and unique electric resistance.

It is also confirmed that it is very effective to regulate the flows of blood and humors in medical treatment by stimulating the unique points by a needle top (Acupuncture), by finger-pressure, or by thermal applications (Moxibution). (See ENCYCLOPEDIA AMERICANA "MEDICINE, 4. CHINESE,HINDU,SEMITIC, AND AMERINDIAN MEDICINE")

Among these methods, the thermal stimulation is practiced by placing suitable quantity of moxa consisting of fibre of mugwort on the skin, igniting the moxa to heat the human body locally and then removing the moxa after suitable time duration. This method of thermal stimulation is objectionable because it is difficult to determine the proper quantity of moxa. In such procedure it is also difficult to determine the proper time for removal of the moxa; and too great a time of application may result in a burn which may leave a lasting scar. Furthermore, the moxibution could not be practiced on inner surfaces of cavities of the human body such as the nasal cavity, mouth or auricular cavity in spite of the fact that various nerves are concentrated there.

SUMMARY OF THE INVENTION

A principal object of this invention is to facilitate moxibution so that any one can readily perform it.

Another object of this invention is to provide an appliance by which moxibution can be practiced at locations within the human body for example the nasal cavity, mouth, auricular cavity etc where conventional moxibution could not previously be practiced.

Still another object of this invention is to improve medical effect of moxibution by adding stimulation due to medical herbs to the thermal stimulation at important points of the human body.

Other features of this invention will be readily apparent from the following description made with reference to the accompanying drawings.

BRIEF DESCRIPTION OF THE DRAWING

FIG. 1 is a sectional view of an embodiment of the present invention, showing a medical appliance.

FIGS. 2a, 2b, 2c and 2d are perspective views of a variety of presser elements which are interchangeably attachable to the appliance according to the part of the body to be treated.

FIGS. 3a, 3b, 3c and 3d are perspective views showing a number of heat-insulating coverings each shaped to fit snugly over a respective one of the presser elements of FIGS. 2a, 2b, etc.

FIG. 3e is a central vertical section through the covering of FIG. 3d; and

FIG. 4 is a partial sectional view illustrating the presser element of FIG. 2d attached to the appliance.

Referring to FIG. 1, there is shown a medical appliance body 1 acting as a hand grip and comprising two split halves 1a and 1b suitably secured together along their meeting edges. An electric heater 2 is arranged inside housing 1 and is controlled by a temperature control mechanism 6 such as a thermostat or a thermistor condenser. This electric heater 2 is in heat exchange contact with a heating plate 5 and is connected to an electric source through a fuse 7, a switch 8 and wires 9.

All presser elements shown in FIGS. 2a through 2d have a base 3 of same size. Each base 3 is provided with a groove 3b on the bottom thereof for receiving the top end of the heating plate 5 to conduct heat from plate 5 to the presser element. The presser element is also provided with a collar 10 which abuts and seats on the upper end of a sleeve 11 formed conjointly by halves 1a and 1b, thus enabling each presser element to be freely interchanged with another element after a cover 12 is removed. It will be noted from FIG. 1 that this cover threadedly engages a reduced threaded portion at the upper end of housing 1.

Each of the presser elements has different top configuration as is shown in FIGS. 2a to 2d according to purposes of use. One of the presser elements shown in FIG. 2a has a slanting top end plane so that it is available for heating various portions in the mouth.

Another presser element shown in FIG. 2b has two stepped rod end so that it is available for heating the nasal cavity.

Still another presser element shown in FIG. 2c has the shape of a rod having larger diameter and a single step, so that it can be safely inserted into the anus.

Still another presser element shown in FIG. 2d has a top end of a gentle slope having a relatively large area so that it may be forced into contact with corresponding areas of the skin such as shoulders and arms.

In use, collar 10 of the presser element is abutted upon the top end seat 11 of the body 1 and then the cover 12 is screwed to the body 1 so that the presser element is secured to the body with an interposed heat-insulator washer or packing 13 made of asbestos etc. This packing prevents the cover 12 from being overheated.

The part 3a of the presser element which contacts the human body is usually covered with a covering 4 of heat-insulator. This ensures that the heat flow from the presser element to the human body, is mild and uniform. Such cover also prevents burning of the flesh.

In general the temperature at the skin is selected at 40° – 50° C or so, the temperature control mechanism 6 being adjusted to gain such temperatures according to the shape of the presser element and the nature of the covering.

The covering 4 may be made of paper, non-woven web, cloth and so on suited to the temperatures of the presser element top end 3a and is shaped into suitable configuration as is shown in FIGS. 3a to 3c.

The covering shown in FIG. 3d is available for application to the skin of the human body and is assembled with the presser element shown in FIG. 2d. As is shown in FIG. 3e which is a sectional view of this covering, suitable medicine which is made by mixing dried garlic, ginger, leek, loquat leaf and so on is sandwiched between two sheets of web 14, 15 which are stitched together. This medicine 16 plays the role of the covering 4 because it has heat-insulation. It also improves the medical effect because of its own effect.

As shown in FIG. 4, the covering 4 may be secured to the body 1 by the cover 12 with the presser element 3 cooperating therewith.

The other coverings shown in FIGS. 3a to 3c may also contain such medicine. On the contrary, in another variant, the covering 4 may be impregnated with an extract of these medicines.

We will now explain how to use this medical appliance.

A suitable presser element is selected according to the portion of the human body to be treated, for example, the presser element shown in FIG. 2a is selected for stomatitis, the element shown in FIG. 2b is for tinnitus or nasal inflammation, or the element shown in FIG. 2c is for hemorrhoids, eyestrain etc, or the element shown in FIG. 2d is for stiffness in the shoulder. After the cover 12 is removed, selected one of the presser elements is attached to the top end of the body 1 in such manner that the groove 3b of the base of the element receives the heating plate 5 and then the cover 12 is attached to the body 1 so that the presser element is clamped through the packing 13. One of the coverings 4 with the medicine 16 or without it is also selected according to the condition of a disease and is installed on the presser element.

Then, the switch 8 is on. After the temperature of the top end 3a of the presser element attains a predetermined value, a user of this appliance forces the top end against the affected part, so that the affected part receives suitable stimulation of heat which makes the circulation of blood and humors more active at the affected part, resulting in activating metabolism.

As another variant, when the user selects the presser element shown in FIG. 2a or FIG. 2b and forces it against outer skin of the human body, it produces the effect of acupuncture because this presser element is usually used for the nasal cavity due to its pointed top. In still another variant, if the presser element of FIG. 2c is used for exerting pressure on the skin, it produces the same effect as finger pressure treatment.

Therefore, the medical appliance according to the present invention ensures safe moxibution without any danger such as a burn even inside various cavities of the human body where application of such treatment have heretofore been impossible, as well as this appliance takes the effect of acupuncture and the effect of finger-pressure and simultaneously the medical effect of medicine.

It will be understood that various other changes and modifications may be made within the scope of the invention without departing from the spirit and scope of the invention. For example, the presser element abovementioned can not be interchangeable but is secured to the body in use for special affected part alone.

What is claimed is:

1. In a medical appliance, a housing having a longitudinal axis and shaped for convenient hand grip, there being an opening disposed in a first end thereof, concentric of said axis, electric heating means within said housing, circuit means for energizing said heating means and including a temperature control therefor, a heat-conducting plate in said housing in heat exchange relation with said heating means and having a part projecting toward and contiguous to said opening, a presser element secured to said housing and having a first portion in contact with the projecting part of said plate and a second portion projecting forwardly through said opening, and first means releasably securing said presser element centrally of and within said opening to obturate the same, said second portion being shaped to contact and treat a selected part of the human body.

2. The appliance of claim 1, said housing having a reduced threaded end coaxially of said axis, said presser element having a flange between its said portions, said first means comprising a centrally-apertured first cover threaded onto the reduced end of said housing and forcing said flange onto the rim of said opening, to obturate the same and enable removal of said presser element on removal of said first cover.

3. The appliance of claim 2, the aperture of said first cover being radially spaced with respect to said axis and from the second portion of said presser element, and a washer of heat-insulating material interposed between said flange and the rim of the aperture of said first cover, to separate them.

4. The appliance of claim 2, the first portion of said presser element being symmetrical about said axis and having an inner end within the housing and a channel in its inner end, transversely thereof, said plate having an end fitting said channel to effect heat exchange with said presser element.

5. The appliance of claim 1, and a cover of flexible heat-insulating material fitting smoothly over and about said second portion of said presser element.

6. The appliance of claim 5, said cover comprising first and second fabric sheets secured in superposed relation, and medicinal material emplaced and confined between said sheets.

7. The appliance of claim 5, said cover conforming to the shape of said second portion of said presser element and smoothly fitting over and about the same.

* * * * *

UNITED STATES PATENT AND TRADEMARK OFFICE
CERTIFICATE OF CORRECTION

PATENT NO. : 4,090,517
DATED : May 23, 1978
INVENTOR(S) : Nagatoki TAKENAKA

It is certified that error appears in the above-identified patent and that said Letters Patent are hereby corrected as shown below:

On cover page the first occurrence of "Nagatoki"

should read -- TAKENAKA -- instead.

Signed and Sealed this

Third Day of October 1978

[SEAL]

Attest:

RUTH C. MASON
Attesting Officer

DONALD W. BANNER
Commissioner of Patents and Trademarks